United States Patent [19]
Grendel et al.

[11] Patent Number: 5,670,128
[45] Date of Patent: *Sep. 23, 1997

[54] REGENERATION OF SULFURIC ACID FROM SULFATE BY-PRODUCTS OF 2-HYDOXY-4-(METHYLTHIO) BUTYRIC ACID MANUFACTURE

[75] Inventors: Robert W. Grendel; Jeffrey B. Klopfenstein; Robin K. Prokop, all of St. Louis, Mo.; Stanley L. Reid, Jonesville, Mich.; J. Michael Willock, St. Louis, Mo.

[73] Assignee: Novus International, Inc., St. Louis, Mo.

[*] Notice: The term of this patent shall not extend beyond the expiration date of Pat. No. 5,498,790.

[21] Appl. No.: 604,410

[22] Filed: Feb. 21, 1996

Related U.S. Application Data

[63] Continuation of Ser. No. 73,877, Jun. 9, 1993, Pat. No. 5,498,790.

[51] Int. Cl.⁶ .................. C01B 17/90; C01B 17/74; C07J 7/00
[52] U.S. Cl. .................. 423/531; 423/522; 423/525; 562/581
[58] Field of Search .................. 423/521, 522, 423/523, 525, 531, 541.4; 562/581; 514/551

[56] References Cited

U.S. PATENT DOCUMENTS

| | | | |
|---|---|---|---|
| 2,655,431 | 10/1953 | Allen, Jr. et al. | 423/522 |
| 2,745,745 | 5/1956 | Blake et al. | 99/4 |
| 2,793,935 | 5/1957 | Haltmeier | 423/531 |
| 3,175,000 | 3/1965 | Gielkens et al. | 260/535 |
| 3,359,069 | 12/1967 | Furkert et al. | 23/178 |
| 3,374,061 | 3/1968 | Topsoe et al. | 423/522 |
| 3,419,601 | 12/1968 | Isbell, Jr. | 260/486 |
| 3,549,320 | 12/1970 | Isbell | 23/168 |

(List continued on next page.)

FOREIGN PATENT DOCUMENTS

| | | |
|---|---|---|
| 0 516 001 A1 | 5/1992 | European Pat. Off. ........ C01B 17/92 |
| 2227878 | 3/1974 | Germany . |
| 60600 | 7/1958 | India . |
| 2190909 | 12/1987 | United Kingdom . |

OTHER PUBLICATIONS

Austin, George T., "Shreve's Chemical Process Industries" (McGraw-Hill, 1984), pp. 340–343, TP145.S5.

Phillips, Tony—"On Site" Alkylation Spent Acid Regeneration Amsterdam, Netherlands, May 30–31, 1991.

Chemical Marketing Reporter, "Degussa Starts Facility to Recycle Sulfuric Acid," Aug. 16, 1982.

V.A. Preobrashenskii and A.M. Flaksman, "Removal of Organic Impurities From Solutions of Sulfuric Acid and Ammonium Sulfate," The Soviet Chemical Industry, 12:3 (1980), pp. 272–276 and 278–280.

(List continued on next page.)

Primary Examiner—Gary P. Straub
Attorney, Agent, or Firm—Senniger, Powers, Leavitt & Roedel

[57] ABSTRACT

A process for the preparation of sulfuric acid by burning the oxidizable components of a feed solution obtained as a byproduct of the preparation of 2-hydroxy-4-(methylthio) butyric acid ("HMBA") by hydrolysis of 2-hydroxy-4-(methylthio)butyronitrile ("HMBN"). A combustion gas containing sulfur dioxide is produced. The combustion gas is cooled to condense water and sulfuric acid, then mixed with a source of oxygen to produce a feed gas containing at least about 0.9 moles oxygen per mole sulfur dioxide. The feed gas is passed over a catalyst for the conversion of sulfur dioxide to sulfur trioxide at a temperature effective for the conversion. Sulfur trioxide may be absorbed in concentrated sulfuric acid to generate additional sulfuric acid which may be recycled and used for hydrolysis of HMBN in the preparation of HMBA. The process may be operated as a closed system in which ammonium bisulfate byproduct of HMBA manufacture is used as the source of sulfur for the generation of sulfuric acid used in the hydrolysis of HMBN to HMBA.

19 Claims, 4 Drawing Sheets

U.S. PATENT DOCUMENTS

| | | | |
|---|---|---|---|
| 3,647,360 | 3/1972 | Jaeger | 23/168 |
| 3,773,927 | 11/1973 | Cummins | 424/166 |
| 3,803,805 | 4/1974 | Low | 55/73 |
| 3,825,657 | 7/1974 | Jenninges | 423/540 |
| 3,954,955 | 5/1976 | Furkert | 423/541 |
| 3,991,047 | 11/1976 | Moudry et al. | 260/239.3 |
| 4,049,646 | 9/1977 | Furkert | 260/239.3 |
| 4,054,562 | 10/1977 | Furkert | 260/239.3 A |
| 4,153,628 | 5/1979 | Gerken et al. | 423/531 |
| 4,177,248 | 12/1979 | Richard | 423/540 |
| 4,208,390 | 6/1980 | Hirabayahsi et al. | 423/356 |
| 4,212,855 | 7/1980 | Kerner et al. | 423/522 |
| 4,256,721 | 3/1981 | Blakey et al. | 423/540 |
| 4,310,690 | 1/1982 | Cummins | 562/581 |
| 4,333,917 | 6/1982 | Dorr et al. | 423/522 |
| 4,376,107 | 3/1983 | Morgenthaler | 423/531 |
| 4,490,347 | 12/1984 | Gelblum | 423/521 |
| 4,524,077 | 6/1985 | Ruest et al. | 514/557 |
| 4,678,655 | 7/1987 | Twardowski | 423/478 |
| 4,912,257 | 3/1990 | Hernandez et al. | 562/581 |
| 5,082,645 | 1/1992 | Al-Samadi et al. | 423/531 |
| 5,498,790 | 3/1996 | Grendel et al. | 473/522 |

OTHER PUBLICATIONS

Author—Unknown—"DSM Develops Process Aiming at Total Oleum Regeneration;" Sulphur, Sep./Oct. 1973, pp. 33.

"TACB/PSD Permit Application Spent Acid Regeneration Plant," filed by Monsanto Company, Oct., 1992.

Rooij, et al., "Caprolactam Without Any Ammonium Sulfate Byproduct," Mar. 18, 1974, Chemical Engineering.

International Search Report for PCT Application PCT/US93/10028, filed Oct. 21, 1993, corresponding to U.S. Patent Application Ser. No. 08/073,877.

Food Chemicals Codex, Third Edition, Washington, D.C., National Academy Press, 1981, pp. xvii–xxv, 1–5, 317–318, 571–574.

REGENERATION OF SULFURIC ACID FROM SULFATE BY-PRODUCTS OF 2-HYDOXY-4-(METHYLTHIO) BUTYRIC ACID MANUFACTURE

This is a continuation of application Ser. No. 08/073,877, filed Jun. 9, 1993 now U.S. Pat No. 5,498,790.

BACKGROUND OF THE INVENTION

This application is directed to a process for disposition of the aqueous sulfate by-product from the manufacture of 2-hydroxy-4-(methylthio)butyric acid and more particularly to a process for regenerating sulfuric acid from the sulfate by-product. The sulfuric acid may be recycled to the 2-hydroxy-4-(methylthio)butyric acid (hereinafter "HMBA") manufacturing process in an essentially closed circuit operation.

The invention is further directed to a process for disposal of HMBA where, for example, that product may be contaminated with adulterating components, or otherwise unsuitable for sale, by use of the HMBA as a sulfur bearing and caloric feed to a spent acid regeneration process.

Ruest U.S. Pat. No. 4,524,077 describes a process for the preparation of a concentrated aqueous solution of HMBA. In this process, the product is produced by sulfuric acid hydrolysis of 2-hydroxy-4-(methylthio)butyronitrile (hereinafter "HMBN") and the resulting hydrolyzate is extracted with a substantially water-immiscible solvent for product recovery. Steam distillation of the extract yields a bottom product comprising the desired concentrated aqueous solution of HMBA. The raffinate from the extract is stripped for recovery of solvent, thereby producing a bottom fraction which comprises a solution of ammonium bisulfate. Depending on hydrolysis conditions, it may also contain some portion of either ammonium sulfate or sulfuric acid, as well as small portions of HMBA. Minor quantities of organic sulfide impurities such as methyl mercaptan, dimethyl sulfide, and dimethyl disulfide are also purged from the process.

Various alternatives exist for disposal of the sulfate by-product solution from the Ruest process. Disposition of this material as an ammonium salt by-product or waste stream results in a substantial consumption of sulfuric acid in the HMBA manufacturing process. Environmental regulations limit the options for waste disposal and generally increase the cost thereof. Although a certain amount of ammonium sulfate can be used as a fertilizer, the modest nitrogen content limits the attractiveness of the by-product salt for this purpose. Moreover, recovery of the sulfate by-product in the form of fertilizer grade ammonium sulfate requires neutralization and purification operations that involve substantial capital and operating expense.

Hernandez et al. U.S. Pat. No. 4,912,257 describes an alternative process for the manufacture of concentrated aqueous solutions of HMBA. Hernandez et al. produces HMBA by essentially the same hydrolysis reaction as Ruest, i.e., by reaction of HMBN with sulfuric acid. Instead of recovering the HMBA product from the hydrolyzate by extraction, Hernandez et al. use the known tendency of the hydrolyzate to separate into aqueous and organic phases as a means for producing an initial separation between HMBA and by-product salt. Hernandez et al. neutralize the hydrolyzate before phase separation so that the aqueous phase withdrawn from the separator contains a high percentage of ammonium sulfate and a relatively small amount of ammonium bisulfate. After phase separation, the aqueous phase is concentrated by evaporation to precipitate a portion of the ammonium sulfate, which is separated by filtration and removed from the process. The filtrate is recycled to the neutralization step.

Although the ammonium sulfate precipitate produced by evaporative concentration of the aqueous phase from the Hernandez et al. phase separation is said to be relatively pure, the market for ammonium sulfate is limited.

Conventionally, therefore, the ammonium bisulfate and ammonium sulfate by-products of HMBA preparation have been largely wasted.

Various processes have long been known for the regeneration of sulfuric acid from certain sulfate bearing waste materials. Isbell et al. U.S. Pat. No. 3,549,320 describes a process for regenerating sulfuric acid from sulfate wastes that are produced in the manufacture of methylmethacrylate ("MMA"). In the process of producing MMA, acetone cyanohydrin is reacted with fuming sulfuric acid to produce methacrylamide sulfate. The methacrylamide sulfate is then reacted with methanol and water to produce MMA and by-product ammonium bisulfate. Other compounds which may be present in the resulting mixture include sulfuric acid, ammonium sulfate, $C_3H_4O(NH_4SO_3)_3$, and organics having the empirical formula $C_3H_{10}O_3$. In the Isbell et al. process, this solution is burned in a flame produced by burning a fossil fuel. The products of combustion include carbon dioxide, oxygen, water, sulfur dioxide, nitrogen, oxides of nitrogen, and a small fraction of sulfur trioxide. The effluent gas is scrubbed, dried, heated to 300°–500° C., and passed over a conversion catalyst in the presence of added amounts of oxygen. The $SO_2$ is catalytically oxidized to $SO_3$, and the $SO_3$ is removed from the gas by absorption in oleum. Further amounts of oleum thereby produced are recycled and used for reaction with further quantities of acetone cyanohydrin in the formation of methacrylamide sulfate.

Gelblum et al. U.S. Pat. No. 4,490,347 describes an improvement in the process of Isbell. Gelblum uses an oxygen-enriched flame in the combustion furnace in order to reduce air requirements, thereby allowing the inert content of the combustion gas to be reduced, and the $SO_2$ content to be increased. Preheating of the air and sulfate solution fed to the furnace further reduces the fuel consumption and the inert fraction, thus further increasing the $SO_2$ gas strength. Gelblum also mentions the alternative of recycling to the furnace a fraction of the stack gas, i.e., the gas exiting the absorber which contains residual portions of sulfur dioxide. The process of Gelblum, like that of Isbell, is specifically directed to the regeneration of sulfuric acid from the sulfate waste of an MMA process.

In addition to the need for disposal of the sulfate waste from a conventional process for the manufacture of HMBA, an occasional need may arise for the disposal of fractions of HMBA itself, for example, HMBA which does not meet published product specifications. HMBA is typically used as an essential amino acid source in the preparation of animal feeds. If an animal feed processor inadvertently mixes the HMBA with other materials not intended for a feed mix, or mixes in the wrong proportions, the HMBA mixture may become unusable, and a need may arise for an economical and environmentally safe method of disposing of the HMBA mixture.

SUMMARY OF THE INVENTION

Among the several objects of the present invention, therefore, may be noted the provision of a process for the disposition of sulfate by-product produced in the preparation of HMBA by hydrolysis of HMBN; the provision of such a process which converts the sulfate by-product to a useful material; the provision of such a process which converts the sulfate by-product to a material which can be used in the manufacture of HMBA; the provision of such a process which allows a substantial reduction in net sulfuric acid requirements for the HMBA manufacturing facility; the provision of such a process which substantially minimizes the volume of by-products which must be removed from the site at which HMBA is manufactured; the provision of such a process which can be operated on an economical basis; and the provision of such a process which is adapted for handling other sulfate wastes in addition to or in combination with the sulfate by-product produced in the manufacture of HMBA.

It is a further object of the present invention to provide a method for disposal of unused HMBA fractions and, in particular, the disposition of such fractions which may be contaminated with adulterating materials that prevent their use in animal feed applications. It is a still further object of the invention to provide a method for disposal of other by-product or purge streams from a manufacturing process for HMBA or a precursor thereof, and of otherwise unusable raw materials, intermediates, or processing aids of such manufacturing process which have sulfur value, fuel value, or both.

Briefly, therefore, the present invention is directed to a process for the preparation of sulfur trioxide. A feed mixture comprising a sulfate feed solution is introduced into a combustion zone in which a fuel is burned with a gas comprising oxygen. The feed solution comprises a solution obtained as a by-product of the preparation of 2-hydroxy-4-(methylthio)butyric acid by the hydrolysis of 2-hydroxy-4-(methylthio)butyronitrile with sulfuric acid, and comprises a sulfate source selected from the group consisting of ammonium sulfate, ammonium bisulfate, sulfuric acid, and mixtures thereof. Oxidizable components in the feed solution are burned in the combustion zone to produce a combustion gas containing sulfur dioxide, carbon dioxide, sulfuric acid vapor, nitrogen, and water vapor. The combustion gas is cooled to condense water and sulfuric acid therefrom, producing a liquid phase comprising a weak sulfuric acid. The weak sulfuric acid is separated from the cooled combustion gas, and oxygen is introduced into the combustion gas to produce a feed gas containing sulfur dioxide containing at least about 0.9 moles of oxygen per mole of sulfur dioxide. The feed gas is passed over a catalyst for the conversion of sulfur dioxide to sulfur trioxide at a temperature effective for the conversion.

The invention is further directed to a process for the preparation of sulfur dioxide in which a feed mixture containing 2-hydroxy-4-(methylthio)butyric acid is introduced into a combustion zone in which a fuel is burned with a gas comprising oxygen. The 2-hydroxy-4-(methylthio) butyric acid is burned with oxygen in the combustion zone to produce a combustion gas containing sulfur dioxide, carbon dioxide, sulfuric acid vapor, and water vapor. The combustion gas is cooled to condense water and sulfuric acid therefrom, producing the liquid phase comprising a weak sulfuric acid. The weak sulfuric acid is separated from the cooled combustion gas, and oxygen is introduced in to the combustion gas to produce a feed gas containing sulfur dioxide containing at least about 0.9 moles of oxygen per mole of sulfur dioxide. The feed gas is passed over a catalyst for the conversion of sulfur dioxide to sulfur trioxide at a temperature effective for the conversion.

Other objects and features will be in part apparent and in part pointed out hereinafter.

BRIEF DESCRIPTION OF THE DRAWINGS

Corresponding reference characters indicate corresponding parts throughout the drawing.

DESCRIPTION OF THE PREFERRED EMBODIMENTS

In accordance with the present invention, it has been found that ammonium bisulfate and ammonium sulfate by-products from the preparation of HMBA by hydrolysis with sulfuric acid can be used as the feed solution in a process for regeneration of the sulfuric acid. The spent acid regeneration process may be integrated with an associated HMBA manufacturing facility to provide a unified system in which acid formed in the spent acid unit provides substantially the entire supply of sulfuric acid for the hydrolysis step of the HMBA process.

Advantageously, other HMBA manufacturing process by-product or purge streams which contain sulfur and/or have fuel value, for example, either high volatility or low volatility purge streams containing organic sulfur compounds, may be fed together with ammonium sulfate or bisulfate solutions to the acid regeneration process. Purge streams from processes for the manufacture of HMBA precursors, such as 3-(methylthio)propionaldehyde ("MMP") may also be included among the materials fed to the acid unit. Feed to the acid unit may further include vent streams from the process and storage vessels of facilities for the manufacture of HMBA and/or its precursors.

A sulfuric acid regeneration unit that is associated and integrated with an HMBA manufacturing facility may also be used for the regular or occasional disposal of other materials that have sulfur or fuel value. For example, where the need exists, the feed to the combustion vessel of the acid regeneration unit may contain raw materials and intermediates for the manufacture of HMBA, processing aids such as extraction solvents or amine catalysts, and derivatives of HMBA such as the calcium salt of HMBA (hereinafter "Ca HMBA").

HMBA itself may also serve as both a fuel and sulfur sources for a sulfuric acid regeneration unit. Thus, the spent acid unit provides a convenient means for disposal of excess, off-specification, or contaminated HMBA. It has been discovered that such a unit may be operated, if and whenever desired, with HMBA as a high proportion of the feed material; in fact, essentially all of the fuel, if desired may be constituted of HMBA. Where a spent acid unit has been designed for optimal integrated operation together with an associated HMBA manufacturing facility, any HMBA to be disposed of may conveniently be fed to the combustion vessel as a minor component, together with a major component of ammonium sulfate or bisulfate solution; or alternatively HMBA may be a primary component of acid regeneration unit feed during periods of shutdown or turnaround of the HMBA manufacturing facility.

In the spent acid regeneration process, ammonium bisulfate or ammonium sulfate solutions, alone or together with other feed materials, are introduced into the combustion furnace of a spent acid recovery unit where they are consumed in a combustion zone produced by burning a fuel, typically a hydrocarbon fuel. At the temperature of the combustion zone, the water content of the feed is vaporized, the sulfuric acid and ammonium sulfate components of the feed are decomposed, ammonia is oxidized to water vapor and nitrogen, and organic sulfur compounds (including any HMBA) oxidized to carbon dioxide, water, $SO_2$, (and $N_2$). The combustion gas is treated for removal of particulates and cooled to condense excess water vapor. By cooling to the extent that the molar ratio of sulfur dioxide to water is approximately 1.0, a gas is produced which can be fed to a sulfuric acid regeneration system for the preparation of concentrated sulfuric acid. If cooled to a temperature at which the $SO_2$ to water vapor ratio is greater than 1.0, the gas may be used in generation of oleum. Optionally, the cooled gas may be dried by contact with concentrated sulfuric acid before it is mixed with air and fed to the catalyst bed of a contact conversion unit. Management of acid cross flows between the absorption and drying system allows the desired concentration to be maintained in each, provided that the $SO_2/H_2O$ molar ratio entering the drying tower is at least about 1.0.

Alternatively, the drying tower may be omitted, and wet gas at an $SO_2/H_2O$ ratio of approximately 1 to 1 or greater can be fed to the contact unit.

Before being passed over the catalyst bed, the cooled and dried combustion gas is mixed with additional air to an oxygen to $SO_2$ ratio between about 0.9 and about 1.2 to provide $O_2$ for oxidation of $SO_2$ to $SO_3$. This gas mixture is then passed over a vanadium or platinum catalyst for the conversion of $SO_2$ to $SO_3$. A temperature of at least about 420° C. is required for the conversion reaction to be initiated. This reaction is highly exothermic; and, as the temperature increases the equilibrium in the reaction $$SO_2 + \tfrac{1}{2}O_2 \rightarrow SO_3$$

becomes increasingly unfavorable. Accordingly, as in a conventional sulfuric acid manufacturing plant, the converter unit is divided into a plurality of catalyst beds, typically three or four, and the gas is cooled between stages to reduce it to a temperature at which the conversion reaction equilibrium is more favorable. If desired, substantial quantities of energy can be recovered, typically in the form of steam, by cooling the gas between catalyst passes in waste heat boilers or heat exchangers for imparting superheat to steam.

The sulfur trioxide bearing gas is contacted with and absorbed by concentrated sulfuric acid in a packed absorption tower or venturi absorber. Sulfur trioxide reacts with water in the absorption acid to produce additional sulfuric acid. The absorption acid is rapidly circulated through the absorber to maintain a relatively low concentration gradient through the tower. As additional sulfuric acid is produced, a side stream is removed from the circulating loop as product acid.

The acid regeneration unit is advantageously integrated with a known process for the manufacture of HMBA, such as that disclosed in the above-mentioned patent of Ruest or that disclosed by Hernandez et al. Acid generated in the spent acid recovery unit is utilized as the hydrolyzing acid in the hydrolysis step of the associated HMBA process, producing further sulfate by-product that is recycled to the spent acid regeneration unit. The feed to the acid unit may also include other by-product or purge streams from the HMBA process, containing organic sulfur compounds, extraction solvents, and the like. Such a combined HMBA/acid regeneration system can operate as an essentially closed system with no net import or export of sulfuric acid except to compensate for physical yield losses. Integration of a facility for the manufacture of HMBA with a sulfuric acid regeneration unit may extend to streams other than sulfuric acid and sulfate by-product. Steam generated in the combustion and absorption steps of the acid unit may be utilized for process heat in the HMBA process. Water from various sources, for example, water vapor condensed from the overhead stream in concentrating the raffinate stripper bottoms, or condensed from the combustion gas of the acid regeneration process, may potentially be reused as process water in the HMBA operation.

Alternatively, the spent acid regeneration unit can be used to process sulfate by-product received from both an HMBA unit and other sources, in which case the respective by-product solutions may either be run alternately through the acid unit or combined and run together. In this instance, energy and water balances may also involve such other sulfate sources, though it is apparent that the extent of integration must be determined on sound engineering principles, balancing the benefits of integration against the operating and start-up constraints they may impose.

In an independent embodiment of the present invention, waste, or unused or unusable HMBA can be disposed of in a spent acid regeneration unit of the type generally described above. In the latter process, the HMBA to be disposed of can be introduced together with sulfate solutions into the combustion zone of the burner vessel of the spent acid unit. HMBA has unique characteristics as a feed material to such a spent acid system. Not only does HMBA have substantial caloric value as a fuel, but it also serves a substantial source of sulfur.

In view of these twin characteristics, HMBA may constitute a high proportion of the fuel that is fed to the burner vessel. In fact, it is feasible to operate the burner with substantially 100% of the combustion heat provided by HMBA. Advantageously, where rapid disposal of excess HMBA is desired, between about 25% and about 100%, preferably between about 40% and about 90% of the fuel required for the combustion step is HMBA. The requisite proportion of HMBA necessary to provide all the fuel combustion of a particular sulfate feed can be readily determined from the composition of the solution and the caloric value of HMBA. Generally, it has been found that the spent acid regeneration unit can be operated with a sulfate feed solution containing between about 0% and about 10% HMBA, for example, 2% to 6%.

Those skilled in the art will recognize that the acceptable proportion of HMBA in the sulfate feed to the burner may be constrained by other limitations. One, for example, is the capacity of a system which must meet the demand for processing of other sulfate by-products. Also consideration may sometimes need to be given to the particular composition of the HMBA material that is fed to the spent acid system. If, for example, the HMBA contains an inorganic chloride material, such as the ammonium chloride produced in the manufacture of HMBA by the process of Cummins U.S. Pat. No. 3,773,927, or if the HMBA is contaminated with chlorinated organic material that yields chlorides upon combustion or pyrolysis, the rate of introduction of HMBA into the combustion zone may be limited by the concentration of chlorides which can be tolerated by the materials of construction of the system.

Raw materials for HMBA, such as 3-(methylthio) propionaldehyde ("MMP"), intermediates used or formed in the Ruest and Hernandez processes, such as HMBN and 2-hydroxy-4-methylthiobutyramide, and products of HMBA, e.g., its various alkali metal, ammonium and alkaline earth metal salts, can also be converted to sulfuric acid, nitrogen, water vapor and $CO_2$ in the spent acid regeneration unit. As indicated above, various purge streams from an HMBA manufacturing process, which commonly contain organic sulfur compounds, may also be used as feed stock for the acid regeneration unit, as may process chemicals used in the manufacture of HMBA and its precursors, e.g., organic amine catalysts and extraction solvents. Specific compositions that may be consumed in the sulfuric acid regeneration process include: HMBA in water with minor organic impurities; Ca HMBA mixtures in water; fractions containing unsalvageable precursor materials such as 2-hydroxy-4-methylthiobutyramide and/or HMBN impurities; MMP and HMBN mixtures with HCN as a minor component; HMBA and ammonium bisulfate mixtures in water with minor organic impurities; purge streams containing methyl mercaptan, dimethyl sulfide, dimethyl disulfide, and HCN; purge streams containing extraction solvent along with organic sulfur compounds; purge streams containing organic amine catalysts such as MMP with minor organic impurities; and combinations of the above.

Figure 1A:
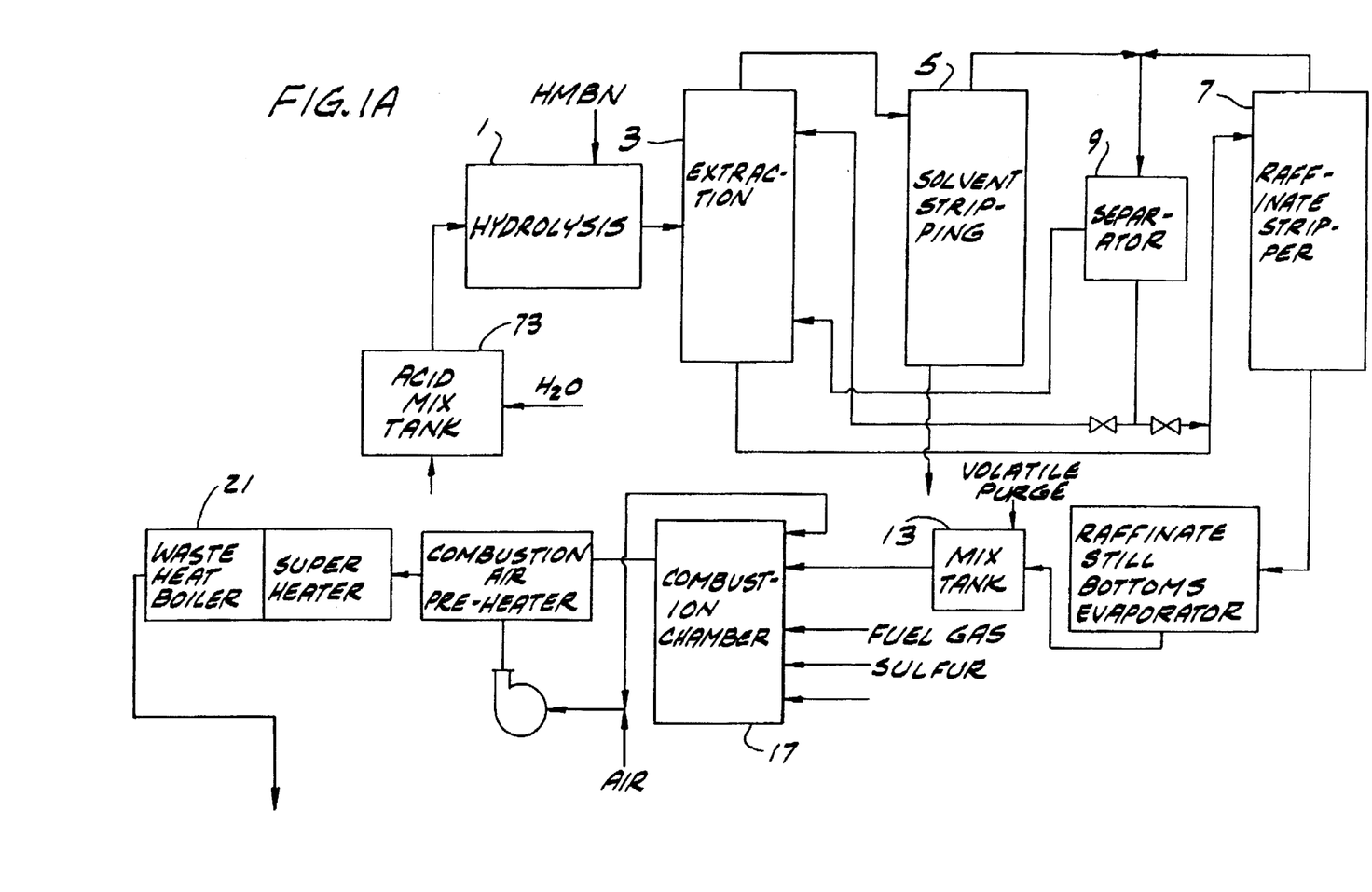
FIGS. 1A, 1B, and 1C together constitute a flow sheet schematically illustrating an integrated HMBA and spent acid regeneration process in which sulfuric acid produced in the regeneration unit is recycled for hydrolysis of HMBN in the manufacture of HMBA.
Figure 1B:
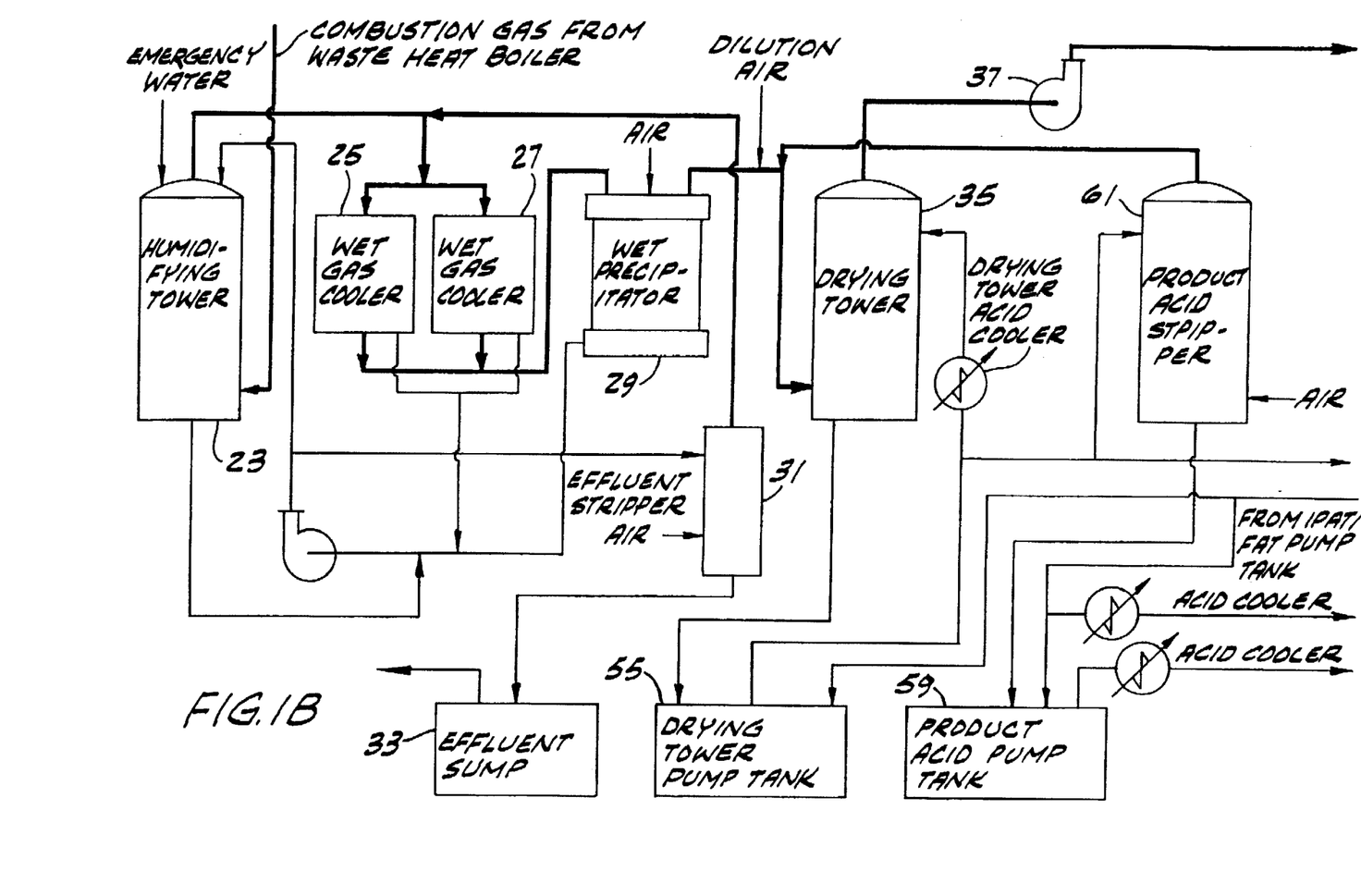
Figure 1C:
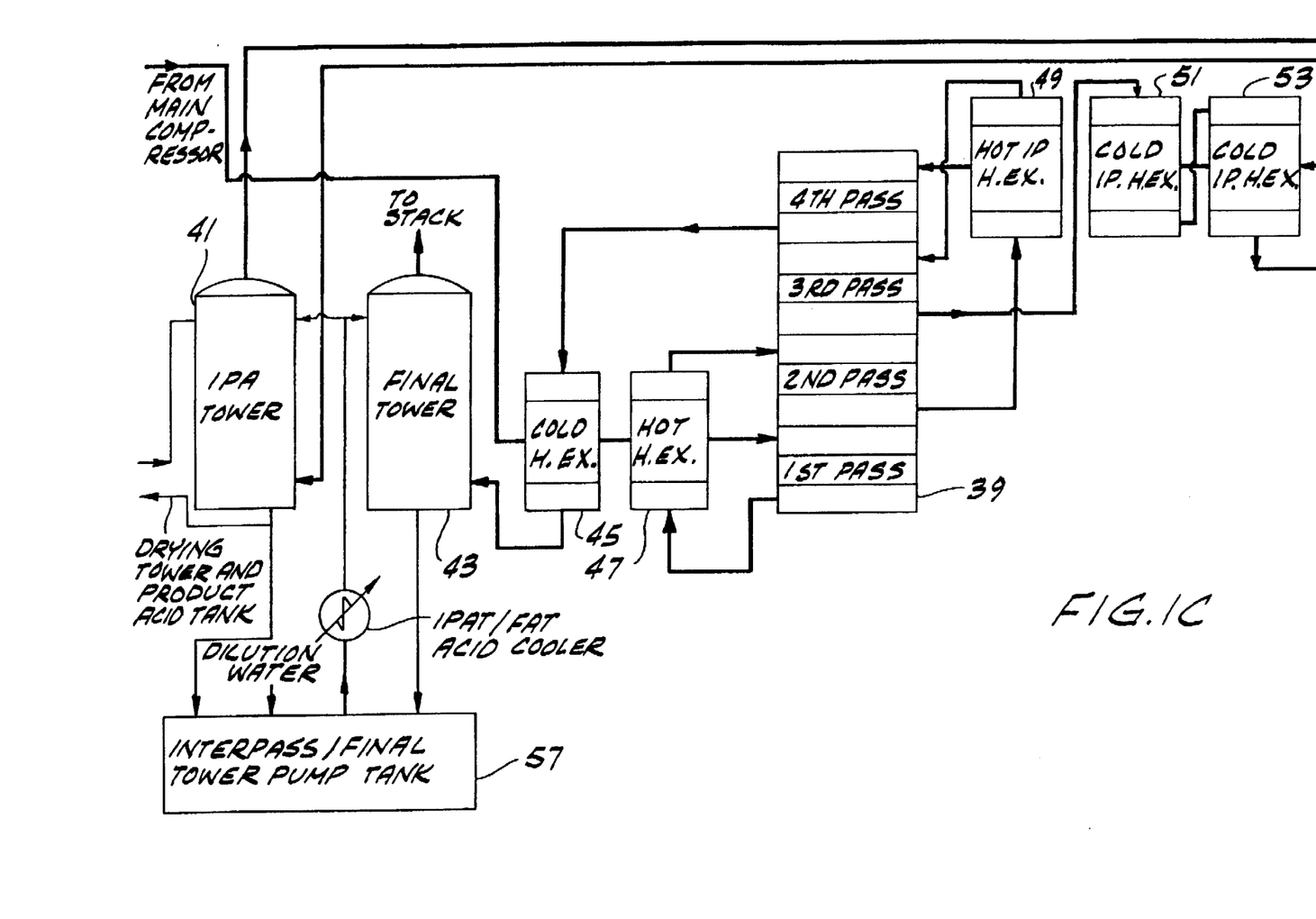

FIGS. 1A, 1B and 1C comprise is a schematic illustration of an integrated process of the invention in which sulfuric acid is used for hydrolysis of HMBN in the manufacture of HMBA by the Ruest et al. process, and the sulfuric acid regenerated from sulfate waste of that process is recycled and used for further hydrolysis. As described in detail in Ruest U.S. Pat. No. 4,524,077, which is expressly incorporated herein by reference, sulfuric acid and HMBN are reacted in a hydrolysis reactor 1 to produce a hydrolyzate containing HMBA, ammonium bisulfate, either ammonium sulfate or sulfuric acid, and traces of various by-products including methyl mercaptan, dimethyl sulfide, dimethyl disulfide, and HCN. The hydrolyzate is contacted with a substantially water immiscible solvent for extraction of HMBA from the aqueous phase, yielding an extract containing a major portion of the HMBA product. As illustrated in FIG. 1A, extraction is conveniently carried out in an extraction column 3 to which hydrolyzate is fed above the mid-point and solvent is introduced near the bottom. Optionally, wash water may be introduced above the feed point for back extraction of ammonium bisulfate and ammonium sulfate salts from the extract. The extract leaves the top of the column and is fed to the upper stages of a steam distillation column 5 which strips the solvent from the extract. A concentrated aqueous solution of HMBA, typically about 85–90% by weight, most preferably about 88% by weight, exits the bottom of the steam distillation column as the HMBA product of the process. The raffinate from the extraction goes to a raffinate stripping column 7 in which an overhead stream of solvent is removed from the aqueous raffinate by steam stripping. Overheads from both HMBA steam distillation column 5 and raffinate stripping column 7 are condensed and directed to a separator 9. In separator 9, the condensate is settled to allow solvent to separate from water. The separated solvent is returned to the bottom of extraction column 3 as the agent for extraction of HMBA from further portions of hydrolyzate.

As shown in FIG. 1A, the aqueous phase may be returned to the top of the extraction column and serve as a back extraction agent for the extract. However, it has been found that the back extraction is not always necessary to achieve desired sulfate levels in the HMBA product. Thus, in a further option that is also shown in FIG. 1A the aqueous phase may be returned to the raffinate stripping column for removal of residual solvent therefrom. In any event, water must ultimately be purged from the process to balance the water introduced into the hydrolysis step and other operations. According to one alternative purge system (not illustrated), the aqueous phase may be directed to a separate stripping column for removal of solvent. In another alternative a membrane separator may be used. In certain alternatives, the residual solvent separated from the aqueous phase may contain organic sulfur compounds which must also be purged from the process. In this instance, the solvent is distilled (or further distilled) for removal of organic sulfur compounds which are advantageously included among the materials fed to the spent acid regeneration unit.

The process illustrated in FIG. 1A does not include an independent step for removal of residual solvent from the aqueous phase, but instead the entire aqueous phase from the separator is directed to the raffinate stripper. Thus, the feed to the raffinate stripper comprises both the raffinate itself, which may contain between about 60% and about 80% by weight ammonium bisulfate, and the aqueous phase from the separator, which contains essentially no sulfates or bisulfates. Since the purpose of stripping the raffinate is not to concentrate the aqueous feed material but simply to remove solvent, the stream leaving the bottom of the raffinate stripper column 7 typically contains between about 45% and about 50% by weight ammonium bisulfate, up to about 5% by weight sulfuric acid or up to about 5% by weight ammonium sulfate, up to about 1% by weight formic and/or acetic acid, and up to about 0.5% by weight HMBA. Raffinate stripper bottoms of such composition are preferably concentrated in a raffinate stripper bottoms evaporator 11 to produce a concentrate having an ammonium bisulfate content of between about 65% and about 85% by weight. For example, the concentrated raffinate stripper bottoms may contain between about 65% and about 85% by weight ammonium bisulfate, up to about 10% by weight sulfuric acid or up to about 10% by weight ammonium sulfate, and up to about 1% by weight HMBA. The evaporation may be carried out at atmospheric or reduced pressure. Because the raffinate stripper bottoms are corrosive, evaporation is preferably carried out under vacuum to minimize the temperature in the vapor/liquid separator and evaporator heat exchanger. Conveniently, the evaporator can be operated at a head pressure of 50 mm Hg absolute to atmospheric, more preferably in a range of about 100 to 400 mm Hg absolute. Advantageously, a multi-effect (typically dual or triple effect) evaporator is used with the first effect at a pressure of 250 to 400 mm Hg and the last effect at a pressure of 100 to 300 mm Hg. Efficiencies in design, construction and operation of an integrated HMBA/spent acid process can be realized if the overhead vapor streams of the HMBA product stripper, raffinate stripper, and raffinate stripper bottoms evaporator (in a multi-effect evaporator, the last effect thereof) are manifolded to a common vacuum system. If the bottoms temperature is maintained below about 120° to 140° C., a zirconium alloy such as Zr 702 may be used for the evaporator heat exchanger. Glass lined equipment may be used for various other components of raffinate bottoms concentrator.

In the alternative embodiment in which the aqueous phase from separator 9 is directed to an independent system for recovery of solvent, the raffinate stripper bottoms has essentially the same sulfate content as the raffinate, i.e., between about 60% and about 70% by weight ammonium bisulfate, up to about 5% by weight sulfuric acid or up to about 5% by weight ammonium sulfate, and up to about 1% by weight HMBA. In this instance, it may be more economical to remove all excess moisture in the spent acid regeneration system and eliminate the capital and operating expense of evaporator 11.

The concentrate from evaporator 11 (or high sulfate content raffinate stripper bottoms) is directed to the sulfuric acid regeneration unit where it forms part or all of the sulfate feed solution. As noted, the feed mixture may also include volatile organic sulfur compounds and other volatile components which are purged from the HMBA production unit. Optional methods for effecting such purge are described hereinbelow. In certain instances, the raffinate stripper bottoms may be blended with some or all of the other constituents of the feed mixture prior to introduction into the combustion zone of the acid regeneration process. FIG. 1A shows a blending tank 13 for this purpose. However, because of immiscibility or other differences in physical or chemical properties, it may not be desirable to blend all such components, but instead introduce different constituent streams through different burner guns into the combustion zone. Whether premixed in the liquid state or mixed only in the combustion zone, an acid regeneration feed mixture derived from the Ruest process typically contains between about 65% and about 85% by weight ammonium bisulfate, up to about 10% by weight sulfuric acid or up to about 10% weight ammonium sulfate, up to about 1% by weight HMBA, up to about 1% by weight methyl mercaptan, up to about 2% by weight dimethyl disulfide, and about 1% by weight HCN.

Feed solution from tank 13 is sprayed into a sulfate solution burner chamber 17, typically from spray heads surrounding a flame produced by burning the hydrocarbon fuel. Different constituent streams of the feed mixture may be introduced through different spray heads. In the combustion zone of chamber 17, the water content of the solution is vaporized, the ammonium sulfate and ammonium bisulfate salts decomposed to $NH_3$, $SO_3$ and water, sulfuric acid vapor decomposed into $SO_3$ and water, and those components containing oxidizable carbon, hydrogen or sulfur are burned. Under combustion conditions, $SO_3$ substantially decomposes to $SO_2$ and $O_2$. Air is introduced into the combustion zone at a rate sufficient to provide between about 0.5% and about 5% oxygen by volume in the gas exiting the combustion chamber. Thus, the combustion gas contains sulfur dioxide, carbon dioxide, water vapor, oxygen and nitrogen.

If the sulfate feed mixture contains nitrates, nitrites, or organic nitrogen compounds, or if the combustion is conducted at high temperature with a substantial excess of air, the combustion gas may also contain oxides of nitrogen. Ordinarily, the concentrated raffinate from the Ruest process does not have any substantial nitrate or nitrite content. However, purge streams from an HMBA process, or from processes for the preparation of precursors, may contain organic nitrogen compounds; and these may be included in the feed mixture to the acid unit. For example, a purge stream from a process for the preparation of MMP may contain a pyridine or triethylamine catalyst.

Formation of oxides of nitrogen may be minimized by carrying out the combustion in two stages. The first stage is run under reducing conditions, i.e., with a slight deficiency of air so that nitriles, ammonia, and any amines contained in the sulfate feed solution, are oxidized to nitrogen gas (and $CO_2$ from nitriles) but not to oxides of nitrogen. The partial combustion gas leaving the first combustion stage contains unburned combustibles and carbon monoxide. To fully convert the carbon, hydrogen and sulfur content of combustibles and carbon monoxide to carbon dioxide, water and $SO_2$, oxidizing conditions are established in the second stage of the combustion by further injection of air. The sum of the air provided to the two stages of combustion is preferably sufficient to provide an oxygen content between about 0.5% and about 5% in the gas leaving the combustion chamber. The combustion gas may contain between about 3% and about 6% $SO_2$, between about 4% and about 8% $CO_2$, between about 0.5% and about 5% $O_2$ and between about 40% and about 60% $N_2$.

This gas exits combustion chamber 17 at a temperature in a range of between about 900° C. and about 1200° C. and is passed through an indirect heat exchanger 19 where heat from the combustion gas is transferred to partially preheated combustion air (preferably above the dew point of the combustion gas) to further preheat the latter e.g., to a temperature of between about 425° C. and about 825° C. Preheating the combustion air reduces the fuel demand necessary to bring the combustion gas to the desired temperature for vaporization of water, decomposition of ammonium salt and sulfuric acid, and activation of ammonia and organic sulfides for combustion. The carbon dioxide and nitrogen content of the combustion gas is accordingly minimized and the $SO_2$ gas strength maximized. Heat from various sources can also be used to preheat the sulfate solution feed stream to the burner.

Gas leaving air preheater 19 passes through a waste heat boiler 21 where the gas is further cooled by generation of high pressure steam, for example, at a pressure of 400 to 1400 psig. Combustion gas exits the air preheater at a temperature in the range of between about 700° and about 800° C. and exits the waste heat boiler at a temperature of between about 300° and about 350° C.

The moisture content of the cooled combustion gas exiting the preheater substantially exceeds the sulfur dioxide content on a molar basis. Typically, the gas also contains particulates. To condition the gas for conversion of $SO_2$ to $SO_3$, excess moisture and particulates must be removed. Conventional gas cleaning steps may be used for this is purpose. In the process of FIG. 1, this accomplished by passage of the gas through a humidifying tower 23, coolers 25 and 27, and an electrostatic precipitator 29.

In humidifying tower 23 (FIG. 1B) the gas exiting the waste heat boiler is quenched with an aqueous scrubbing liquid to further cool the gas and scrub particulates from it. Tower 23 is preferably of open interior configuration wherein aqueous scrubbing liquid descends as a spray and as a film along the interior walls. Contact with the combustion gas flowing up through the column causes cooling of the gas and transfer of particulates to the aqueous phase. Sulfuric acid vapor in the gas is condensed and removed with the particulates in the aqueous phase discharged from tower 23.

The gas stream leaves scrubber 23 essentially saturated with moisture at a temperature in the range of between 70° and about 80° C. From tower 23 the gas passes in series through indirect exchangers 25 and 27, in which the gas is cooled to a temperature between about 35° and about 45° C. causing condensation of a substantial fraction of the water vapor in the gas. Typically, additional particulates are removed from the gas with this condensate, which may further contain minor additional quantities of sulfuric acid.

The gas exiting coolers 25 and 27 enters an electrostatic precipitator 29 where remaining particulates are removed along with aqueous mist entrained from coolers 25 and 27. The weak acid condensate from tower 23, coolers 25 and 27, and precipitator 29 is collected, passed through an effluent stripper 31 where residual $SO_2$ is removed by stripping with air. A portion of the weak acid is used as the scrubbing liquid in humidifying tower 23, and the remainder is discharged to effluent sump 33. Weak acid to the sump has a concentration of 1-2% by weight sulfuric acid. Air from effluent stripper 31 containing residual $SO_2$ is recycled to humidifying tower 23.

Figure 2:
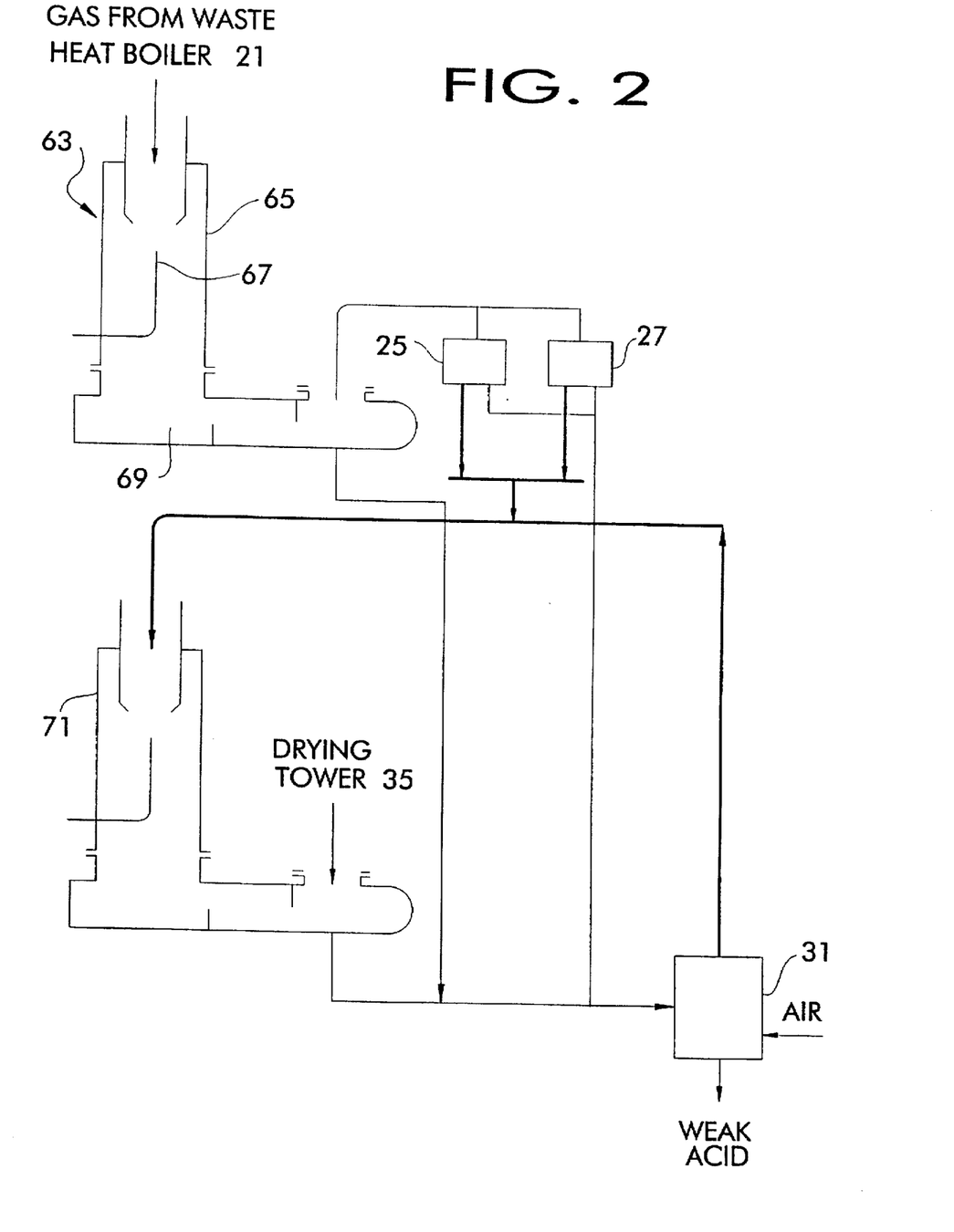
FIG. 2 illustrates an alternative scheme for removing particulates and reducing the water content of the combustion gas before conversion of $SO_2$ to $SO_3$ in the process of FIGS. 1A, 1B and 1C.

An alternative system for conditioning the gas is illustrated in FIG. 2. Gas exiting the air preheater is passed through a reverse jet scrubber 63 where the gas is quenched to a temperature of between about 70° C. and about 80° C. and scrubbed for removal of particulates by contact with a reverse jet of water. In scrubber 63, the gas flows downwardly through a conduit 65 into which a jet of aqueous scrubbing liquid is injected upwardly through a nonrestrictive orifice 67 at a velocity sufficient to furnish greater than 1.0 horsepower of energy per square foot of the cross-sectional area of the conduit. The average gas velocity through the conduit is at least 1000 feet per minute, and in excess of the flooding velocity. The gas collides with the liquid, forcing liquid radially outward toward the conduit wall. This creates a zone of high turbulence at the gas/liquid interface, and the flows are balanced and the equipment sized to create a standing wave turbulence zone through which the gas must pass. The system operates at a high liquid to gas flow ratio and with negligible atomization, so that subsequent gas/liquid separation is readily accomplished. Gas and liquid are separated in an entrainment separator 69. Such reverse jet scrubbers are described in U.S. Pat. No. 3,803,805, which is expressly incorporated herein by reference, and are available from Monsanto Enviro-Chem Company under the trade mark DYNA-WAVE®.

Gas leaving entrainment separator 69 is passed sequentially through gas coolers 25 and 27, where the gas is cooled to between about 35° C. and about 45° C., causing condensation of a substantial fraction of the water vapor in the gas. Additional particulates are removed in this condensate. Gas leaving cooler 27 is passed through another reverse jet scrubber 71 for final removal of particulates. The structure and operation of scrubber 71 are essentially identical to those of scrubber 63. Particulate laden scrubbing liquid and weak acid condensate from coolers 25 and 27 are collected and passed through an effluent stripper 31. Preferably, a fraction of the weak acid stream is diverted ahead of the effluent stripper and used as the scrubbing liquid in reverse jet 63. Scrubbing liquid for reverse jet 71 is provided by circulation of condensate from coolers 25 and 27 an/or fresh water makeup to the system. In lieu of coolers 25 and 27, a direct contact packed tower may be provided in which the gas is cooled and dehumidified by a circulating stream of weak acid.

The gas leaving electrostatic precipitator 29 or reverse jet scrubber 71 comprises the feed to a conventional contact process sulfuric acid manufacturing process. As illustrated in FIG. 1B, the gas may first be contacted with sulfuric acid in countercurrent drying tower 35. Dry gas leaving tower 35 passes through main compressor 37 to converter 39. As shown in FIG. 1C, converter 39 (FIG. 1C) contains up to four passes of a vanadium pentoxide (e.g., a Cs-activated $V_2O_5$) catalyst for conversion of $SO_2$ to $SO_3$. Conversion gas exiting the third stage of converter 39 is passed through an interpass absorption tower 41 where $SO_3$ in the gas is absorbed in concentrated sulfuric acid. Removal of the $SO_3$ by this means helps drive the $SO_2$ to $SO_3$ conversion forward in the fourth pass of converter 39. Gas exiting the fourth pass is contacted countercurrently with concentrated sulfuric acid in final absorbing tower 43. Gas exiting tower 43 is released to the atmosphere, though it may be subject to further treatment for removal of residual $SO_2$.

Before entering the first pass of converter 39, the gas is heated by passing it first through an indirect heat exchanger 45, where its temperature is raised by transfer of heat from gas exiting the fourth stage, and then through an indirect heat exchanger 47, where its temperature is further increased by transfer of heat from gas exiting the first catalyst stage. The gas from the first pass which has been cooled in heat exchanger 47 is directed to the second pass and thence to the third pass through an indirect heat exchanger 49 where it is cooled by transfer of heat to gas returning to the fourth pass from interpass absorption tower 41. Gas from the second pass which has been cooled in heat exchanger 49 is directed to the third pass and from thence to the interpass absorption tower via a pair of indirect heat exchangers 51 and 53 where it flows countercurrently to gas returning from the interpass tower; and heat is transferred from the former gas stream to the latter. After $SO_3$ is absorbed in the interpass tower, the gas is returned to the fourth pass of the converter by flowing in series through heat exchangers 53, 51 and 49. Gas exiting the fourth pass is cooled by transfer of heat to first pass feed gas in heat exchanger 45 and then directed to final absorption tower 43.

Referring to FIG. 1B, acid is circulated over drying tower 35 from a drying tower acid pump tank 55. As the drying tower acid progressively absorbs moisture from the cooled combustion gas stream, a side stream of acid sufficient to remove an equivalent amount of water is removed from the circulating acid stream and then divided into two streams, one of which is directed to the interpass absorption tower, the other of which is directed to a product acid pump tank 59. As shown in FIG. 1B acid is circulated over both interpass tower 41 and final tower 43 from an interpass final tower pump tank 57. As sulfuric acid is produced in these towers the water and acid material balance is maintained by transferring an equivalent amount of acid to drying tower pump tank 55 and/or a product acid pump tank 59.

Drying tower acid transferred to product acid tank 59 is first passed through a product acid stripper 61 (FIG. 1B). In the product acid stripper, air is blown through the acid and packed tower for removal of residual $SO_2$ therefrom. The acid exiting the bottom of the product acid stripper enters product acid pump tank 59 and the air is blended in with the gas entering drying tower 35.

Preferably the acid strength maintained in the circulating loop between drying tower 35 and drying tower pump tank 55 is about 93% to 96% by weight, while the acid strength in the circulating loops between pump tank 57 and absorption towers 41 and 43 is about 98.5% to 100% by weight. Where highly concentrated acid product is desired, it may be removed from the line in which acid is otherwise transferred from pump tank 57 to pump tank 59. The remainder of the net production of 98.5% to 100% acid in the circulating loops of the interpass and final absorption towers is transferred to pump tank 59 where it is blended with 93% to 96% acid from the drying tower loop to yield product acid of 95–97%. In an integrated HMBA/spent acid plant, acid is usually not withdrawn from the transfer line between pump tank 57 and pump tank 59. Instead, all of the acid, at a strength of 95–97%, is returned to a mix tank 73 where it is diluted with water to the proper strength for delivery to hydrolysis vessel 1. As disclosed in the above-mentioned patent of Ruest, sulfuric acid having a strength of greater than about 50% by weight on an organic free basis is suitable for hydrolyzing HMBN to HMBA.

Where the only ultimate source of sulfur in the sulfate feed solution is the sulfuric acid charged to hydrolysis vessel 1, the sulfuric acid produced in the spent acid regeneration unit exactly balances the acid requirements of the hydrolyzer at steady state conditions and constant production rate, except consequential losses of operation such as, e.g., the acid contained in the weak acid stream from the effluent stripper, minor amounts of sulfate in the HMBA product, and other yield losses. Thus, the system of FIGS. 1A to 1C can be operated as an integrated unit for the hydrolysis of HMBN to HMBA and regeneration of fresh sulfuric acid from the by-product sulfate stream without the need to export sulfuric acid. Additional sulfuric acid is added only to compensate for yield losses in operation of the system.

Alternatively, the system depicted in FIG. 1A to 1C can be operated to process sulfate wastes from other sources which are fed to the burner either alternately to sulfate waste from the HMBA process or combined therewith.

For example, the sulfate waste obtained from the HMBA process may be combined with sulfate waste from the manufacture of acrylonitrile to provide the sulfate feed stream processed in the sulfuric acid generation unit. A typical feed stream comprising combined effluents from both the HMBA and acrylonitrile processes contains between about 35% and about 45% by weight ammonium bisulfate, up to about 5% by weight sulfuric acid, between about 15% and about 20% by weight ammonium sulfate, up to about 1% methylmercaptan, up to about 1% dimethyl sulfide, up to about 1% dimethyl disulfide, and up to about 1% HCN. In such operation, the amount of sulfuric acid generated over a significant operating cycle exceeds the requirements of the HMBA process. However, the spent acid regeneration unit can be integrated with a plurality of manufacturing units which utilize sulfuric acid. There are numerous organic manufacturing processes in which sulfuric acid is used but does not become part of the principal product of the process, instead serving only as a catalyst, hydrolyzing agent, or neutralizing agent for alkaline by-products. A plurality of such processes can be integrated with a sulfuric acid regeneration unit to produce a closed system which may be operated without substantial export or import of sulfuric acid.

As mentioned above, in the manufacture of HMBA, it is common to remove one or more purge streams containing compounds such as methyl mercaptan, dimethyl sulfide, dimethyl disulfide, and HCN. Frequently, such a purge stream is removed in a liquid/vapor separation step such as distillation, and may be drawn from that step as either the light end or heavy end, more commonly the former. Such a fraction is advantageously fed to the combustion chamber of the sulfuric acid regeneration unit where it serves both as a source of sulfur and a fuel.

Various measures may be taken to purge volatile sulfur compounds from the process. For example, the hydrolyzate may be stripped under vacuum to provide a hydrolysis stripping stream in which the volatile impurities are concentrated. This stream may be directed immediately to the combustion chamber of the sulfuric acid regeneration unit or may, for example, be condensed and combined with the concentrated raffinate stripper bottoms to comprise the sulfate feed solution to the burner. Where volatiles are stripped from the hydrolyzate, water vapor is removed with the volatile organic materials and appears in the condensate. If the hydrolysis stripping condensate is to be combined with the concentrated raffinate stripper bottoms to comprise the feed to the burner, the raffinate stripper bottoms are preferably concentrated to a relatively high degree in raffinate evaporator 11, for example, up to about 82 to 86% by weight ammonium bisulfate so that, when it is combined with the hydrolysis stripping condensate, the resultant feed solution to the combustion chamber has the preferred strength of between 70 and 80% by weight. Those skilled in the art will recognize that the hydrolysis condensate should not be combined with the raffinate stripper bottoms before concentration of the latter since the volatiles will be removed in the vapor phase if present during the evaporative concentration of the raffinate stripper bottoms.

In another alternative embodiment of the invention, the solvent recovered from steam distillation of the extract and stripping of the raffinate is distilled to remove the volatile organic sulfide impurities. The overheads condensate from this stripping operation comprises a solution of volatile organics in the solvent. Typically, this condensate contains between about 30 and about 70% by weight of a water immiscible solvent, between about 0.1% and about 5% by weight methylmercaptan, between about 1% and about 6% dimethyl sulfide, between about 25% and about 10% dimethyl disulfide, and between about 0.1% and about 2% HCN. Since it has quite high caloric value, this overheads condensate is useful as both a fuel and sulfur source for the spent acid regeneration unit. In this embodiment, it is unnecessary to concentrate the raffinate stripper bottoms to an ammonium bisulfate concentration of greater than about 75–80% by weight in evaporator 11. Where the water phase from separator 9 is independently disposed of, it may be economically preferable to dispense with the evaporation step entirely.

Among the alternative sulfate sources which may be used as the feed solution to the spent acid regeneration unit of FIG. 1 is the ammonium sulfate solution produced upon phase separation of the hydrolyzate in the process of Hernandez et al. U.S. Pat. No. 4,912,257. This composition differs from that of the Ruest process in that the ammonium salt is predominantly sulfate and contains very little bisulfate. Generally, the aqueous phase obtained from the Hernandez process contains between about 40% and about 50% by weight ammonium sulfate, and between about 0% and about 5% by weight ammonium bisulfate. Although the phase separation provides substantial separation of HMBA from ammonium salt, the HMBA content is significant. While the aqueous phase from the phase separation might otherwise be used directly as the sulfate feed solution to the combustion chamber, economics ordinarily dictate proceeding with evaporative concentration of the aqueous phase, as taught by Hernandez et al., to precipitate a major fraction of the ammonium sulfate and produce a supernatant liquor that can be separated by filtration and recycled to the phase separation step for maximum recovery of HMBA. The precipitated salt is redissolved in water to provide a feed solution to the combustion chamber. Advantageously, the salt may be redissolved in the overheads condensate from the aqueous phase evaporator, thus eliminating the need for other arrangements for disposal of this excess process water.

Where there is a market for ammonium sulfate, a portion of the precipitate may be diverted for that purpose, and any excess directed to the spent acid recovery unit. If it is not necessary to prepare fertilizer or other commercial grade ammonium sulfate, the filter cake obtained by filtering or centrifuging the slurry from the aqueous phase concentrator need not be of high purity. This may affect the optimal extent of dewatering and washing of the filter cake.

Because the sulfate liquor from the Hernandez et al. process contains a high ratio of sulfate to bisulfate, the solubility limit is much lower than for the sulfate wastes of the Ruest process, and the maximum strength solution that may be fed to the combustion chamber is correspondingly lower. The strength of the solution and the greater hydrogen content of ammonium sulfate have a calculable impact on fuel demand, oxygen demand and $SO_2$ gas strength. For maximum efficiency, the solution should be as close to the saturation limit as possible. If an ammonium sulfate precipitate can be produced in sufficiently fine particulate form to be susceptible to combustion, it may be feasible to redissolve the precipitate in a deficiency of water and feed a slurry to the burner. However, this is generally not preferred because of line plugging, settling, combustion inefficiencies, etc. Despite these complications, the process illustrated in FIG. 1 and described hereinabove may be readily adapted to the regeneration of sulfuric acid from the Hernandez et al. by-product stream.

In view of the above, it will be seen that the several objects of the invention are achieved and other advantageous results attained.

As various changes could be made in the above methods without departing from the scope of the invention, it is intended that all matter contained in the above description and shown in the accompanying drawing shall be interpreted as illustrative and not in a limiting sense.

What is claimed is:

1. A process for the manufacture of feed grade 2-hydroxy-4-(methylthio)butyric acid in a facility for said process using sulfuric acid recycled from a spent acid recovery unit that is associated with said facility, the process comprising:

hydrolyzing 2-hydroxy-4-(methylthio)butyronitrile with sulfuric acid, thereby producing 2-hydroxy-4-(methylthio)butyric acid and by-products selected from the group consisting of ammonium sulfate, ammonium bisulfate, sulfuric acid, and mixtures thereof;

introducing into a combustion zone of said spent acid recovery unit a feed mixture comprising a sulfate feed solution containing a sulfate source comprised of said by-products;

burning a fuel and oxidizable components of said feed solution in a combustion zone with a gas comprising oxygen to produce a combustion gas containing sulfur dioxide, carbon dioxide, nitrogen, and water vapor, said feed solution being contacted in a first stage of said combustion zone with a reducing flame in which ammonia, nitriles and any amines released from the solution are oxidized to produce nitrogen gas and any oxides of nitrogen are reduced to nitrogen gas, thereby producing a partial combustion gas substantially free of oxides of nitrogen, said partial combustion gas being contacted with additional gas containing oxygen to oxidize unburned fuel and any carbon monoxide in the partial combustion gas, thereby producing said combustion gas;

introducing oxygen into said combustion gas to produce a feed gas containing sulfur dioxide and at least about 0.9 moles of oxygen per mole of sulfur dioxide;

passing said feed gas over a catalyst for the conversion of sulfur dioxide to sulfur trioxide at a temperature effective for said conversion;

thereafter contacting the gas that has been passed over said catalyst with sulfuric acid for the absorption of sulfur trioxide and the formation of sulfuric acid;

recycling sulfuric acid formed by said absorption to said facility for the manufacture of 2-hydroxy-4-(methylthio)butyric acid;

purging sufficient water from the process such that the strength of said recycled sulfuric acid is greater than about 50% by weight on an organic free basis; and contacting said recycled sulfuric acid with 2-hydroxy-4-(methylthio)butyronitrile for the preparation of feed grade 2-hydroxy-4-(methylthio)butyric acid.

2. A process as set forth in claim 1 wherein said sulfate feed solution contains at least one compound selected from the group consisting of 3-(methylthio)-propionaldehyde, HCN, 2-hydroxy-4-(methylthio)butyronitrile and an organic amine catalyst for the conversion of 3-(methylthio)-propionaldehyde to 2-hydroxy-4-(methylthio)butyronitrile.

3. A process as set forth in claim 1 wherein said feed mixture comprises between about 65% and about 85% by weight ammonium bisulfate, up to about 10% by weight sulfuric acid, up to about 10% by weight ammonium sulfate, up to about 10% by weight 2-hydroxy-4-(methylthio)butyric acid, above 0% to about 1% by weight methyl mercaptan, above 0% to about 1% by weight dimethyl sulfide, above 0% to about 2% by weight dimethyl disulfide, and above 0% to about 1% by weight HCN.

4. A process as set forth in claim 1 wherein:

2-hydroxy-4-(methylthio)butyronitrile is hydrolyzed with sulfuric acid to produce a hydrolyzate containing 2-hydroxy-4-(methylthio)butyric acid and ammonium bisulfate;

the hydrolyzate solution is contacted with a substantially water-immiscible organic solvent in a liquid/liquid extraction system to produce an extract containing 2-hydroxy-4-(methylthio)butyric acid and a raffinate containing ammonium bisulfate; and said feed solution comprises ammonium bisulfate from said raffinate.

5. A process as set forth in claim 4 wherein said raffinate is stripped for removal of residual extraction solvent, the raffinate stripper bottoms are concentrated by evaporation, and said feed solution comprises the resulting concentrate.

6. A process as set forth in claim 5 wherein water removed in the concentration of said raffinate stripper bottoms is recycled and used as process water in the preparation of 2-hydroxy-4-(methylthio)butyric acid by hydrolysis of 2-hydroxy-4-(methylthio)butyronitrile.

7. A process as set forth in claim 5, wherein said combustion gas is cooled without condensation in a waste heat boiler by generation of steam to which heat is transferred from said combustion gas.

8. A process as set forth in claim 7 wherein steam generated by transfer of heat from said combustion gas is used for process heat in said facility for the manufacture of 2-hydroxy-4-(methylthio)butyric acid.

9. A process as set forth in claim 7 wherein steam generated in said waste heat boiler is used as a source of heat in producing a concentrated 2-hydroxy-4-(methylthio) butyric acid solution from said hydrolyzate.

10. A process as set forth in claim 4 wherein said raffinate is stripped for removal of residual extraction solvent, and said feed solution comprises unconcentrated raffinate stripper bottoms.

11. A process as set forth in claim 4 wherein the extract obtained from said extraction is distilled to remove the solvent and produce a concentrated aqueous solution of 2-hydroxy-4-(methylthio)butyric acid; and said solvent is recycled to the extraction step and contacts further hydrolyzate for extraction of further 2-hydroxy-4-(methylthio) butyric acid.

12. A process as set forth in claim 1 wherein 2-hydroxy-4-(methylthio)butyronitrile is hydrolyzed with sulfuric acid to produce a hydrolyzate containing 2-hydroxy-4-(methylthio)butyric acid and ammonium bisulfate;

said hydrolyzate is neutralized with ammonia and allowed to separate into an organic phase containing the major portion of said 2-hydroxy-4-(methylthio)butyric acid and an aqueous phase containing ammonium sulfate; and said feed solution contains ammonium sulfate from said aqueous phase.

13. A process as set forth in claim 12 wherein said aqueous phase is concentrated by evaporation and said feed solution comprises the resulting concentrate.

14. A process for the preparation of sulfuric acid comprising the steps of:

introducing a feed mixture comprising a sulfate feed solution into a combustion zone in which a fuel is burned with a gas comprising oxygen, said sulfate feed solution comprising a by product of a process for the preparation of 2-hydroxy-4-(methylthio)butyric acid by hydrolysis of 2-hydroxy-4-(methylthio)butyronitrile with sulfuric acid to produce a hydrolyzate solution containing 2-hydroxy-4-(methylthio)butyric acid and a sulfate source selected from the group consisting of ammonium sulfate, ammonium bisulfate, sulfuric acid, and mixtures thereof, said sulfate feed solution comprising said sulfate source, said feed mixture further comprising volatile organic sulfur compounds that have been purged from said process for the preparation of 2-hydroxy-4-(methylthio)butyric acid, said volatile organic sulfur compounds comprising precursors of 2-hydroxy-4-(methylthio)butyric acid or by-products of the preparation of 2-hydroxy-4-(methylthio)butyric acid or its precursors, oxidizable components of said feed solution being burned in said combustion zone to produce a combustion gas containing sulfur dioxide, carbon dioxide, nitrogen, and water vapor, said sulfate feed solution being contacted in a first stage of said combustion zone with a reducing flame in which ammonia, nitriles and any amines released from the solution are oxidized to produce nitrogen gas and any oxides of nitrogen are reduced to nitrogen gas, thereby producing a partial combustion gas substantially free of oxides of nitrogen, said partial combustion gas being contacted with additional gas containing oxygen to oxidize unburned fuel and any carbon monoxide contained in the partial combustion gas, thereby producing said combustion gas;

introducing oxygen into said combustion gas to produce a feed gas containing sulfur dioxide and at least about 0.9 moles of oxygen per mole of sulfur dioxide;

passing said feed gas over a catalyst for the conversion of sulfur dioxide to sulfur trioxide at a temperature effective for said conversion; and thereafter contacting the gas that has been passed over said catalyst with sulfuric acid for the absorption of sulfur trioxide and the formation of sulfuric acid.

15. A process as set forth in claim 14 wherein said organic sulfur compounds are purged during preparation of 2-hydroxy-4-(methylthio)butyric acid by separation during said hydrolysis or from said hydrolyzate solution.

16. A process as set forth in claim 15 wherein the preparation of 2-hydroxy-4-(methylthio)butyric acid comprises:

contacting said hydrolyzate solution with a substantially water-immiscible organic solvent in a liquid/liquid extraction system to produce an extract containing 2-hydroxy-4-(methylthio)butyric acid and a raffinate containing ammonium bisulfate;

separating solvent from said extract and said raffinate; and separating organic sulfur compounds from said solvent, said feed mixture introduced into said combustion zone comprising an aqueous solution containing sulfate of said raffinate and organic sulfur compounds separated from said solvent.

17. A process as set forth in claim 16 wherein the preparation of 2-hydroxy-4-(methylthio)butyric acid further comprises:

separating an aqueous phase containing residual solvent from said recovered solvent;

separating said residual solvent from said aqueous phase; and removing organic sulfur compounds from said residual solvent, said feed mixture introduced into said combustion zone further comprising organic sulfur compounds removed from said residual solvent.

18. A process for the manufacture of 2-hydroxy-4-(methylthio)butyric acid in a facility for said process using sulfuric acid recycled from a spent acid recovery unit that is associated with said facility, the process comprising:

hydrolyzing 2-hydroxy-4-(methylthio)butyronitrile with sulfuric acid to produce 2-hydroxy-4-(methylthio) butyric acid and a by-product sulfate solution;

introducing into a combustion zone of said spent acid recovery unit a feed mixture comprising said by-product sulfate solution and 2-hydroxy-4-(methylthio)butyric acid;

burning a fuel and 2-hydroxy-4-(methylthio)butyric acid contained in said by-product sulfate solution in a combustion zone with a gas comprising oxygen to produce a combustion gas containing sulfur dioxide, carbon dioxide, nitrogen, and water vapor, said feed solution being contacted in a first stage of said combustion zone with a reducing flame in which ammonia, nitriles and any amines released from the solution are oxidized to produce nitrogen gas and any oxides of nitrogen are reduced to nitrogen gas, thereby producing a partial combustion gas substantially free of oxides of nitrogen, said partial combustion gas being contacted with additional gas containing oxygen to oxidize unburned fuel and any carbon monoxide in the partial combustion gas, thereby producing said combustion gas; introducing oxygen into said combustion gas to produce a feed gas containing sulfur dioxide and at least about 0.9 moles of oxygen per mole of sulfur dioxide;

passing said feed gas over a catalyst for the conversion of sulfur dioxide to sulfur trioxide at a temperature effective for said conversion;

thereafter contacting the gas that has been passed over said catalyst with sulfuric acid for the absorption of sulfur trioxide and the formation of sulfur acid;

recycling sulfuric acid formed by said absorbtion to said facility for the manufacture of 2-hydroxy-4-(methylthio)butyric acid;

purging sufficient water from the process such that the strength of said recycled sulfuric acid is greater than about 50% by weight on an organic free basis; and contacting said recycled sulfuric acid with 2-hydroxy-4-(methylthio)butyronitrile for the preparation of 2-hydroxy-4-(methylthio)butyric acid.

19. A process as set forth in claim 18 wherein between about 25% and about 100% of the combustion heat is provided by combustion of 2-hydroxy-4-(methylthio) butyric acid.

* * * * *